US012667253B2

(12) United States Patent
Mikaelian et al.

(10) Patent No.: US 12,667,253 B2
(45) Date of Patent: Jun. 30, 2026

(54) AUTOMATED VISION TESTING

(71) Applicant: Hedgefog Research, Inc., San Pedro, CA (US)

(72) Inventors: Gareguin Mikaelian, San Pedro, CA (US); Jae H. Choi, San Pedro, CA (US); Alexander Van Atta, Cincinnati, OH (US)

(73) Assignee: Hedgefog Research, Inc., San Pedro (CA)

( * ) Notice: Subject to any disclaimer, the term of this patent is extended or adjusted under 35 U.S.C. 154(b) by 287 days.

(21) Appl. No.: 18/492,686

(22) Filed: Oct. 23, 2023

(65) Prior Publication Data

US 2024/0130613 A1     Apr. 25, 2024
US 2024/0225437 A9     Jul. 11, 2024

Related U.S. Application Data

(60) Provisional application No. 63/418,437, filed on Oct. 21, 2022.

(51) Int. Cl.
*A61B 3/032*     (2006.01)
*A61B 3/00*     (2006.01)
*A61B 3/08*     (2006.01)

(52) U.S. Cl.
CPC ............ *A61B 3/032* (2013.01); *A61B 3/0008* (2013.01); *A61B 3/0025* (2013.01); *A61B 3/08* (2013.01); *A61B 2560/0223* (2013.01)

(58) Field of Classification Search
CPC ..... A61B 3/032; A61B 3/0008; A61B 3/0025; A61B 3/08; A61B 2560/0223; A61B 3/0091; A61B 3/024; A61B 3/028; A61B 3/066; A61B 3/085; A61B 3/022
USPC ......................................................... 351/243
See application file for complete search history.

(56) References Cited

U.S. PATENT DOCUMENTS

| | | | |
|---|---|---|---|
| 2012/0068998 A1* | 3/2012 | Hong ................... | H04N 13/144 345/419 |
| 2012/0075586 A1* | 3/2012 | Kirschen ............... | A61B 3/028 351/239 |
| 2016/0157711 A1* | 6/2016 | Maddalena ............ | A61B 3/032 351/241 |
| 2018/0140178 A1* | 5/2018 | Anderson .............. | A61B 3/024 |
| 2021/0386285 A1* | 12/2021 | Walsh ...................... | A61B 3/18 |
| 2022/0013228 A1* | 1/2022 | Gonzalez Garcia . | A61B 3/0025 |

* cited by examiner

*Primary Examiner* — Mohammed A Hasan
(74) *Attorney, Agent, or Firm* — Chang & Hale LLP

(57)     ABSTRACT

This application discloses systems and methods for auto-mated vision testing. Performing automated vision testing can be beneficial in a number of eye care applications due to the reduction of chair time, increase of the measurement accuracy, elimination of human errors, capability for internal instrument calibration, and the possibility for test standard-ization.

20 Claims, 10 Drawing Sheets

Mirror

Screen

Concave
mirror

Virtual image

*1001*

*1002*

AUTOMATED VISION TESTING

CROSS-REFERENCE TO RELATED APPLICATIONS

This application claims priority to U.S. Prov. App. No. 63/418,437 filed Oct. 21, 2022 and entitled "SYSTEMS AND METHODS FOR AUTOMATED VISION TESTING," which is expressly incorporated by reference herein in its entirety for all purposes.

BACKGROUND

Field

This disclosure is in the general area of vision examination including but not limited to visual acuity, contrast sensitivity, color vision, motion sensitivity, accommodation range and speed, and binocular vision function including but not limited to stereo acuity, horizontal exophoria, horizontal esophoria, vertical heterophoria, suppression, vergence range, exotropia, and esotropia.

Description of Related Art

Despite recent tremendous leaps in the development of new technologies for image recording, presentation, manipulation, 3D capabilities, and analysis, many vision exams are still performed using paper Snellen charts, paper color charts, and Amsler grids. Some projection systems are used, such as the NIDEK CP-770 chart projector, or in the case of a limited exam room space, the NIDEK SSC-370 space-saving chart. For technology-based color vision testing, the Konan ColorDX instrument is available, which relies on color isolation and threshold-based testing.

SUMMARY

According to a number of implementations, the present disclosure relates to the vision testing including visual acuity, contrast sensitivity, color vision, motion sensitivity, accommodation range and speed, and binocular vision function including but not limited to stereo acuity, horizontal exophoria and esophoria, vertical heterophoria, suppression, vergence range, exotropia, and esotropia.

According to a first aspect, the present disclosure relates to a system or an instrument for performing vision examination of a patient or a subject.

In some embodiments of the first aspect, visual stimuli are presented to the subject and the subject is asked to identify the visual stimuli.

In some embodiments of the first aspect, the subject specifies the identified stimuli using a keyboard input system.

In some embodiments of the first aspect, the subject specifies the identified stimuli using a gamepad controller input system.

In some embodiments of the first aspect, the subject specifies the identified stimuli using a custom input system with one or several buttons or a touchscreen input system.

In some embodiments of the first aspect, the subject specifies the identified stimuli by notifying the instrument operator of which stimuli the subject sees, can see, identifies, or can identify.

In some embodiments of the first aspect, the disclosed system automatically detects which stimuli can the subject see by detecting and analyzing the motion of the subject's eyes.

In some embodiments of the first aspect, stimuli can be presented to the left, right, or both eyes of the subject.

In some embodiments of the first aspect, the stimulus presented to the right eye can be different from the stimulus presented to the left eye.

In some embodiments of the first aspect, a stereo image is formed by presenting different images to the left and right eye of the subject.

In some embodiments of the first aspect, shutters can be used to present different images to the left and right eye.

In some embodiments of the first aspect, the shutters can be liquid crystal (LC) shutters.

In some embodiments of the first aspect, the patient is asked to fuse moving stimuli by crossing or uncrossing the eyes of the patient.

In some embodiments of the first aspect, the presented stimuli have a shape of the Landolt C.

In some embodiments of the first aspect, the presented stimuli have a shape of letter E.

In some embodiments of the first aspect, the presented stimuli are concentric rings.

In some embodiments of the first aspect, the presented stimuli are static.

In some embodiments of the first aspect, the presented stimuli are dynamic.

In some embodiments of the first aspect, stimuli can be varied in size, contrast, or color contrast.

In some embodiments of the first aspect, the color of the stimulus and the background can be selected in such a way to only excite a single cone type in the subject's eye.

In some embodiments of the first aspect, the presented stimulus is dependent on the subject's identification of the previous stimuli.

In some embodiments of the first aspect, psychometric functions are used to determine which stimuli are to be presented next.

In some embodiments of the first aspect, vision examination comprises of a number of vision tests.

In some embodiments of the first aspect, the instrument can be configured to present stimuli at different viewing distances.

In some embodiments of the first aspect, there can be two or three viewing distances, including but not limited to near, intermediate, and far.

In some embodiments of the first aspect, the instrument can be comprised of actuated optical elements, by actuation of which different viewing distance configurations can be achieved.

In some embodiments of the first aspect, the actuation of the optical elements can be performed manually.

In some embodiments of the first aspect, the actuation of the optical elements can be performed automatically.

In some embodiments of the first aspect, the optical elements can be flat or curved mirrors, liquid crystal shutters, lenses, or prisms.

In some embodiments of the first aspect, the operator may create an examination protocol by arranging different vision tests in order.

In some embodiments of the first aspect, the individual vision tests can be performed at different viewing distances.

In some embodiments of the first aspect, the scores of the vision tests can be recorded and displayed on the operator's screen.

In some embodiments of the first aspect, the stimuli and subject's responses can be recorded and displayed on the operator's screen.

In some embodiments of the first aspect, the estimate of the psychometric function can be recorded and displayed on the operator's screen.

In some embodiments of the first aspect, the test results can be calculated and reported after the completion of the test.

In some embodiments of the first aspect, the test results can be calculated and reported during the performance of the test.

In some embodiments of the first aspect, the stimuli can be presented using a display screen.

In some embodiments of the first aspect, the stimuli can be presented using a projector.

In some embodiments of the first aspect, the stimuli can be presented using more than one projector with overlapping images.

In some embodiments of the first aspect, a calibration sensor can be positioned in line with the projector or behind the calibration screen.

In various aspects, the present disclosure relates to a system for performing automated vison testing, the system comprising: a display device system configured to present one or more stimuli to one or both eyes of a tested subject; an input device configured to record responses of the tested subject; and an analysis system configured to analyze the responses and to present a result of the vision test being performed.

In some embodiments, the system further includes one or more optical components, wherein a plurality of stimuli viewing distances is achieved by arranging the system with different configurations of the one or more optical components. In some embodiments, at least one of the one or more optical components is a curved mirror. In some embodiments, the one or more optical components includes a second mirror, an optical path of the one or more stimuli including the curved mirror or the second mirror by actuating the curved mirror or the second mirror into and out of the optical path, and wherein a viewing distance of the system changes as a consequence of which mirror is in the optical path of the one or more stimuli. In some embodiments, the second mirror is a flat mirror. In some embodiments, at least one of the one or more optical components is a flat mirror that is configured in a manner so that it can be rotated about an axis, the axis parallel to the surface of the flat mirror.

In some embodiments, the display device system includes one or more projection devices and a front projection screen, the one or more projection devices configured to project images onto the front projection screen. In some embodiments, the system further includes a calibration sensor located behind the front projection screen, wherein the front projection screen is configured in such way that at least a portion of the light from the one or more projection devices passes through the front projection screen and is detected by the calibration sensor. In some embodiments, the calibration sensor is a photodiode. In some embodiments, the calibration sensor is a colorimeter. In some embodiments, the calibration sensor is a spectrometer. In some embodiments, the calibration sensor is configured to be used for calibration verification of the system or for performing an automated self-calibration of the system. In some embodiments, the one or more projection devices includes a first projection device and a second projection device, the first projection device configured to project a large field image and the second projection device configured to project a small field image. In some embodiments, the large field image and the small field image overlap. In some embodiments, the one or more projection devices includes a first projection device and a second projection device, the first projection device configured to have a first value of maximum brightness and the second projection device configured to have a second value of maximum brightness that is different from the first value of maximum brightness.

In some embodiments, the system further includes optical shutters positioned in front of an eye of the tested subject. In some embodiments, the optical shutters are liquid crystal shutters.

In various aspects, the present disclosure relates to a method of generating a high color resolution image, the method comprising projecting two overlapping images onto a screen, the two overlapping images projected by more than one projection system, each projection system having a different maximum brightness value.

In various aspects, the present disclosure relates to a method for vergence testing of a human subject, the method comprising displaying a first stimuli to a left eye of the human subject and a second stimuli to a right eye of the human subject, the first stimuli different from the second stimuli, the first and second stimuli configured in a way that they can be identified by the human subject only when the human subject is correctly fusing the first and second stimuli from the left and right eye.

In some embodiments, the first and second stimuli are stereo stimuli.

For purposes of summarizing the disclosure, certain aspects, advantages and novel features have been described herein. It is to be understood that not necessarily all such advantages can be achieved in accordance with any particular embodiment. Thus, the disclosed embodiments can be carried out in a manner that achieves or optimizes one advantage or group of advantages as taught herein without necessarily achieving other advantages as can be taught or suggested herein.

DETAILED DESCRIPTION OF SOME EMBODIMENTS

The headings provided herein, if any, are for convenience only and do not necessarily affect the scope or meaning of the claimed subject matter.

Overview

Despite recent tremendous leaps in the development of new technologies for image recording, presentation, manipulation, 3D capabilities, and analysis, many vision exams are still performed using paper Snellen charts, paper color charts, and Amsler grids. Some projection systems are used, such as the NIDEK CP-770 chart projector, or in the case of a limited exam room space, the NIDEK SSC-370 space-saving chart. For technology-based color vision testing, the Konan ColorDX instrument is available, which relies on color isolation and threshold-based testing. Current vision testing procedures are time-consuming, labor-intensive, potentially subject to transcription errors, and vulnerable to "test preparation" or coaching, which may compromise the integrity of the test. Automated vision testing may enable medical practitioners to more accurately track the health of patients through the use of threshold estimates, rather than pass/fail criteria for each aspect of vision. A vision testing system that includes acuity, color, ocular motility (e.g., hyperphoria, hypophoria esophoria, exophoria, hypertropia, hypotropia, esotropia, and/or exotropia), stereo vision examination, and other tests can be very beneficial addition to the exam capabilities at optometric and ophthalmic practices.

Figure 1:
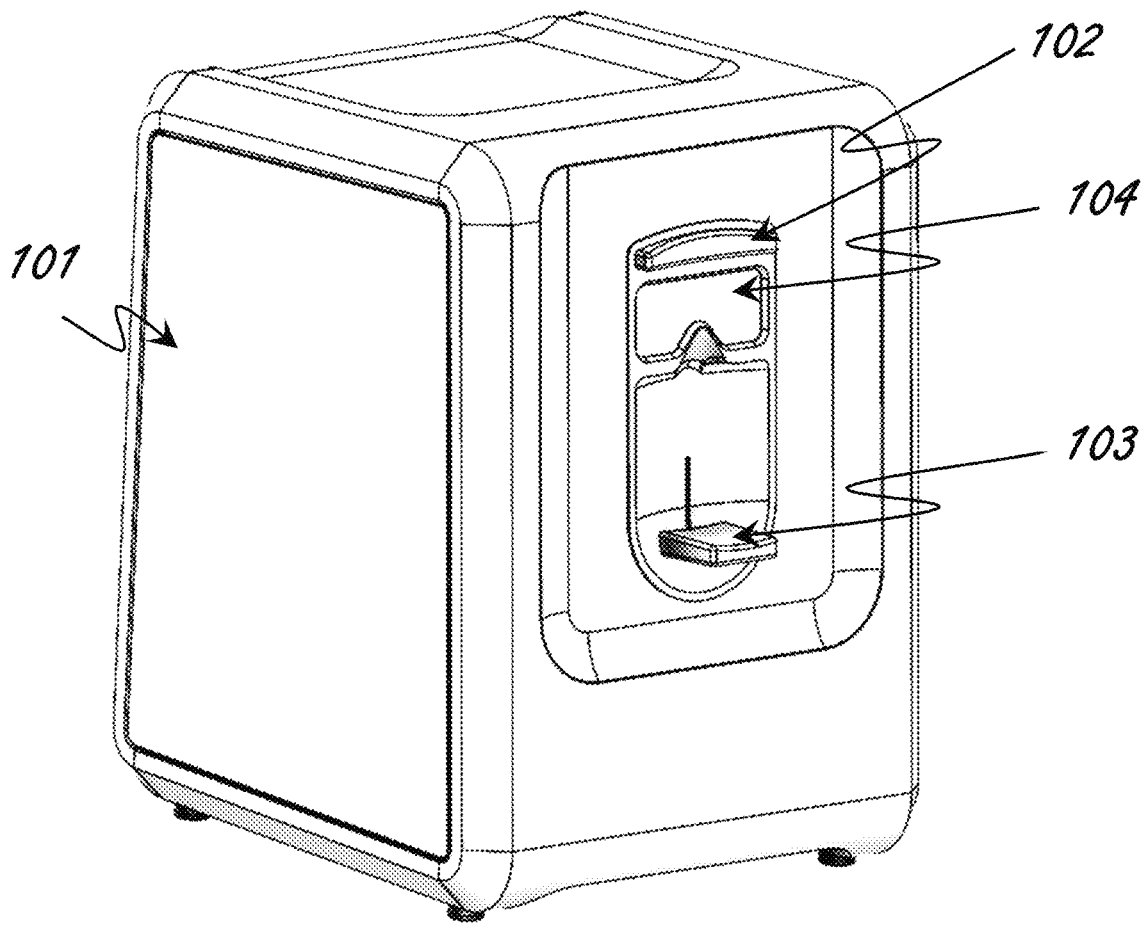
FIG. 1 illustrates an exemplary embodiment of a tabletop vision testing device.

The systems and methods described herein are intended for performing a comprehensive visual examination at an optometry or ophthalmology office. FIG. 1 illustrates a schematic diagram of an example instrument 101 for performing an automated visual examination. The instrument 101 is a compact device that can fit on a standard instrument table often found in the optometrist's office. The instrument 101 includes a forehead rest 102, a chin rest 103, and a viewport 104.

In general, the patient positions their forehead against the forehead rest 102 and their chin on the chin rest 103. The patient then looks into the viewport 104 at the visual stimuli presented on a screen or monitor (not shown) located inside the instrument 101. The instrument 101 can have one or more configurations for vision testing at different distances such as near, intermediate, far, and others. Switching between configurations can be done by mechanically moving internal optical components, reorienting projectors, using different display methods, or any combination of the above. Switching between different configurations for vision testing can be performed automatically using internal actuators or manually with the use of levers and handles, for example.

The instrument 101 can be configured to perform a variety of visual examinations including, but not limited to, visual acuity, contrast sensitivity, color contrast, horizontal and vertical phoria, ocular motility, stereo acuity, binocular vision, retinal testing for AMD, visual field evaluation, and other tests that can be used to characterize the vision of a patient or a research subject. The instrument 101 can be configured to operate by utilizing threshold algorithms, where the size, contrast, or other parameter of the visual stimulus is dependent on the previous responses by the patient or a study subject. The test outputs can be in terms of scores, psychometric curves, list of responses, or any other means that can be descriptive of the results of a given test.

In some implementations, the test can be performed using conventional vision testing algorithms. For example, the patient can be asked to read a line presented to them and the exam administrator may verify that the line is read correctly. The instrument 101 can be used for vision testing, various professional qualifications, or as endpoints in clinical trials. Advantageously, a combined near, intermediate, and far distance vision examination can be advantageous for evaluating the efficacy of various endpoints for presbyopia managing modalities.

In some embodiments, it can be advantageous to equip the instrument 101 with a gaming controller, joystick, or a keyboard for recording responses from a patient. In certain embodiments, it can be advantageous to have a speech recognition interface that recognizes verbal responses from the patient.

The instrument 101 can be configured to perform a number of vision tests, some of which are summarized herein.

Example Vision Test: Visual Acuity Test

In some implementations, a visual stimulus can be presented on a background and the subject can be asked to identify the stimulus. The feedback from the subject can be recorded and analyzed. Generally, stimulus and background luminance may remain the same throughout the test, but the stimulus size may change. One example of a stimulus can be a Landolt C oriented in different directions. In such a case, the subject can be asked to identify the orientation of the Landolt C.

Example Vision Test: Contrast Sensitivity Test

In some implementations, a stimulus can be presented on a background and the subject can be asked to identify the stimulus. The feedback from the subject can be recorded and analyzed. Generally, stimulus and background luminance as well as the stimulus size may change, but the stimulus and background color may remain the same.

Example Vision Test: Color Contrast Sensitivity Test

In some implementations, a stimulus can be presented on a background and the subject can be asked to identify the stimulus. The feedback from the subject can be recorded and analyzed. Generally, stimulus and background luminance and color, as well as the stimulus size may change.

Example Vision Test: Stereo Acuity Test

In some implementations, a stereo stimulus can be presented to both eyes and the subject can be asked to identify the shape or the configuration of the stimulus based on the stereo presentation. The feedback from the subject can be recorded and analyzed. The stimulus presentation time can be limited.

Example Vision Test: Fusion Range Test

In some implementations, a series of stereo images can be presented to both eyes of the subject. The subject can be asked to determine the moment the images cannot be fused any longer. In another example of a fusion range test, a first dot can be presented to both eyes while a second dot can be transiently presented to one or the other eye located on the right or on the left of the first dot. The subject can then be asked to identify on which side of the first dot the second dot was present. A correct answer can be indicative of a successful fusion. In yet another example of a fusion range test, a stereo stimulus can be presented to the subject. The subject can be able to identify the stereo stimulus if the images in the right and left eyes are fused properly. The state of the subject's fusion can be determined by knowing if the subject is correctly identifying the stereo stimuli.

Example Vision Test: Dynamic Stereo Acuity Test

In some implementations, a series of stereo images can be presented to both eyes of the subject at the same time. The subject can be asked to move a joystick or another input device. The motion of the input device may influence the stereo image sequence. An error between the subject's control device position and the optimal position can be recorded and analyzed at a given time interval.

Example Vision Test: Spatial Rotation Test

In some implementations, an image can be presented for a known time interval. The subject can be asked to classify the image. The subject's response can be recorded and analyzed.

Example Vision Test: Motion Perception Test

In some implementations, a series of images can be presented to the subject. The subject can be asked to classify the series of images by the direction of motion or rotation. The subject's response can be recorded and analyzed.

Example Vision Test: Ocular Motility Test

In some implementations, a series of stimuli can be presented in a sequence to both eyes or to one of the eyes. The gaze direction can be measured using one or several eye tracking cameras. The gaze direction for each stimulus presentation can be reported and analyzed.

Multiple Viewing Distances

The instrument 101 can advantageously be configured to test vision at multiple viewing distances in a single instrument. In some implementations, the instrument 101 can utilize one or more mirrors to test the patient's or subject's vision at various viewing distances. These mirrors can be fixed or the mirrors can be actuated using manual or powered actuators. It can be advantageous to implement a plurality of viewing distances that are conventionally used in vision measurements. For example, the plurality of viewing distances can include a first distance for near vision measurements, a second distance for intermediate vision measurements, and a third distance for far vision measurements. In some embodiments, the near vision distance can be about 16-inches, the intermediate vision distance can be about 32-inches, and the far vision distance can be about 20-feet or 6-meters. In certain embodiments, it may be beneficial to test the far vision at a shorter distance (e.g., about 3 meters or about 4 meters).

Figure 2:
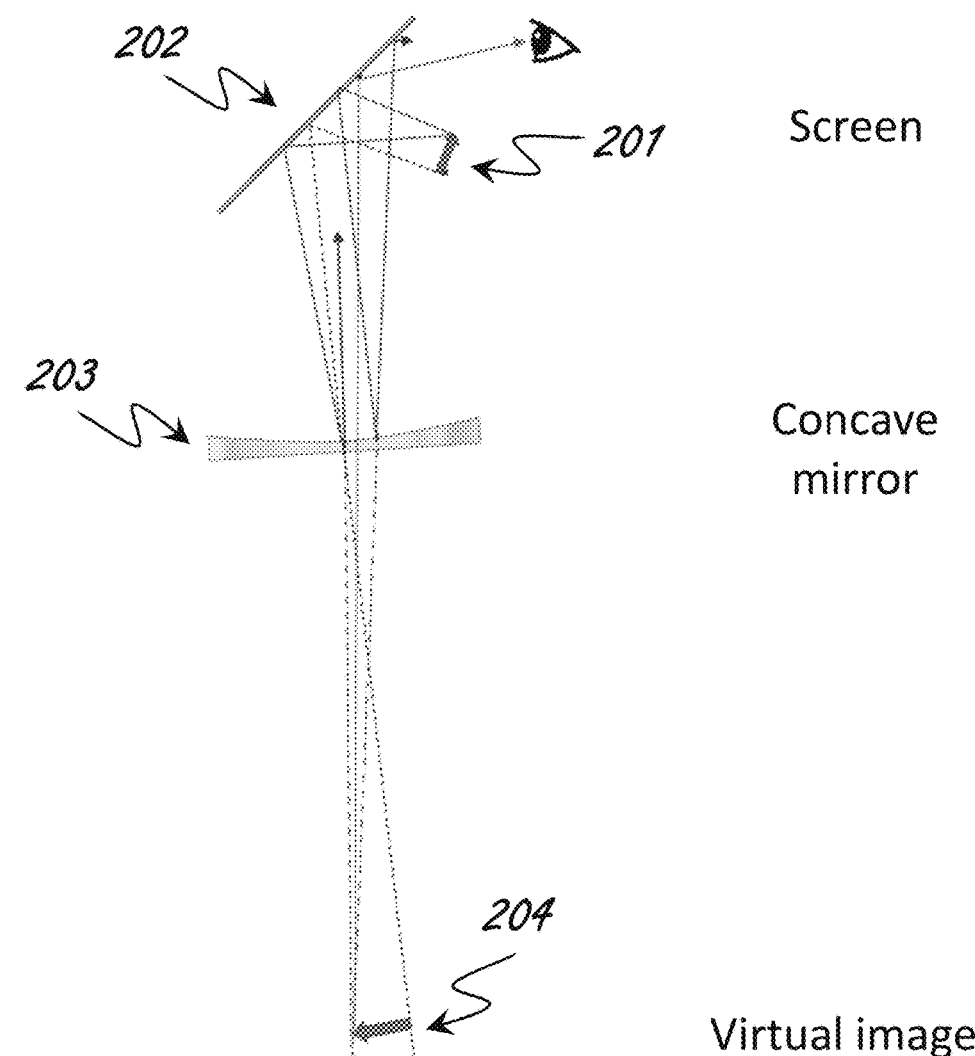
FIG. 2 illustrates an optical arrangement using a curved mirror for far vision testing.

FIG. 2 illustrates an example configuration for achieving a far viewing distance in a compact device (e.g., such as the instrument 101 of FIG. 1). The image of a stimuli on a screen 201 or a monitor is reflected from a flat mirror 202 onto a curved mirror 203 (e.g., a concave mirror). As a result, a virtual image 204 is formed at a far viewing distance and the patient sees the image as a far object. In some implementations, the instrument 101 includes the screen 201, the flat mirror 202, and the curved mirror 203. In certain implementations, the instrument 101 also includes a projector (not shown) to project the stimuli on the screen 201. In certain implementations, the screen 201 is capable of generating an image of the stimuli without a projector (e.g., when the screen 201 is a monitor or other display device capable of generating an image without a projector).

Figure 3:
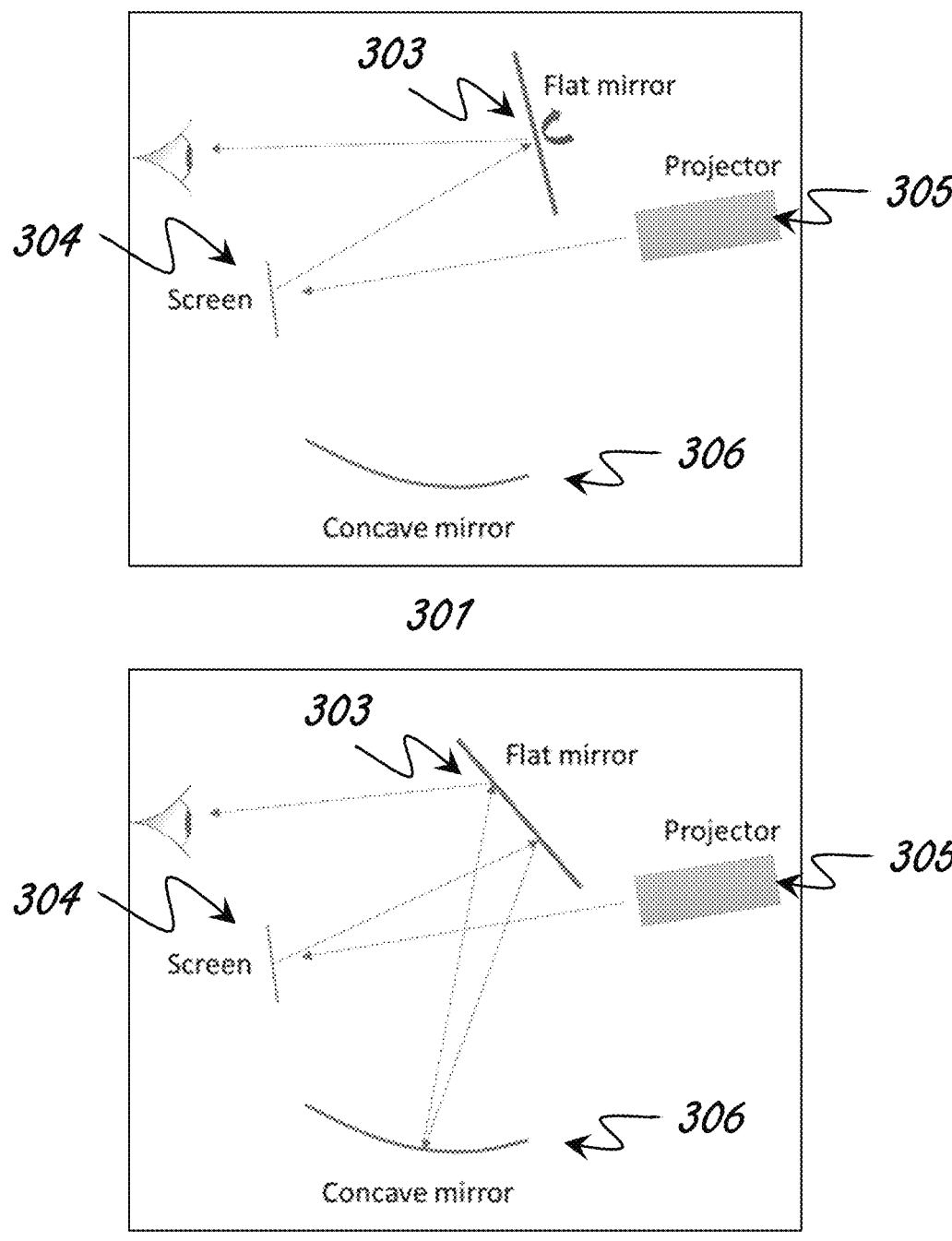
FIG. 3 illustrates two possible configurations of the instrument for near and far vision testing.

Variations of this configuration can be used in combination with other mirrors and beam splitters to achieve multiple viewing distances. For example, FIG. 3 illustrates two potential configurations that include a near viewing distance configuration 301 and a far viewing distance configuration 302. Each configuration utilizes a flat mirror 303, a screen 304, a projector 305, and a curved mirror 306. The configurations 301, 302 differ by the angle of the flat mirror 303 (similar to the flat mirror 202 of FIG. 2). In the near viewing distance configuration, the flat mirror 303 is angled to present an image of the screen 304, wherein the screen presents an image of a stimuli as provided by the projector 305. In the far viewing distance configuration, the flat mirror 303 is angled to reflect an image from the screen 304 onto the curved mirror 306 to present a virtual image (not shown) to the patient, similar to the configuration of FIG. 2. Again, these configurations can be implemented in a compact device, such as the instrument 101. In such instances, the instrument 101 includes the flat mirror 303, the screen 304, the projector 305, and the curved mirror 306. In some embodiments, the projector 305 and screen 304 can be replaced by a monitor or other display device capable of generating an image without a projector.

Figure 4:
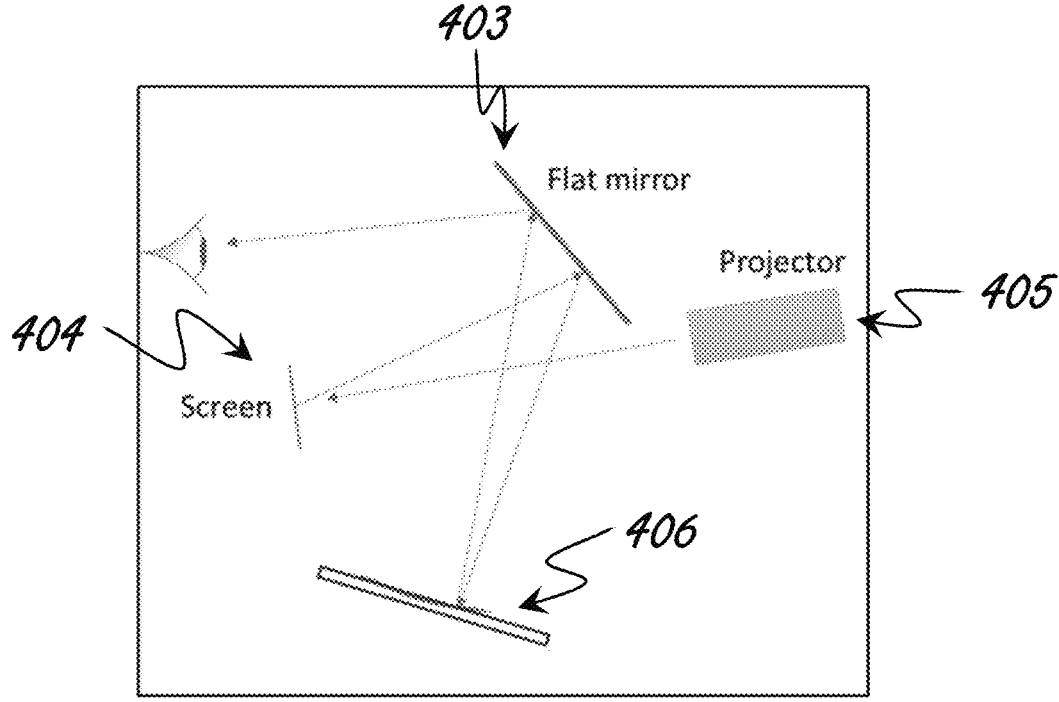
FIG. 4 illustrates an example of a configuration of an instrument for intermediate distance vision testing.

FIG. 4 illustrates another configuration that can provide an intermediate viewing distance by using a second flat mirror 406 in a location similar to the curved mirror 303 of FIG. 3. Thus, the configuration includes a first flat mirror 403 (similar to the flat mirror 303 of FIG. 3), a screen 404 (similar to the screens 201, 304), a projector 405 (similar to the projector 305), and the second flat mirror 406. The addition of the second flat mirror 406 to the configuration increases the length of the optical path between the screen and the patient to provide an intermediate viewing distance for vision testing. The configuration of FIG. 4 can be implemented in a compact device, similar to the instrument 101 of FIG. 1.

In some embodiments, the configurations of FIGS. 3 and 4 can be combined in a single instrument. For example, the second flat mirror 406 of FIG. 4 can be positioned above or below the curved mirror 303 of FIG. 3 and the instrument can include a translation mechanism to switch the instrument's configuration between intermediate and far viewing distances. When such a translation mechanism is combined with a rotation mechanism of the curved mirror 303, near, intermediate, and far configurations can be achieved in a single, compact device, such as the instrument 101 of FIG. 1.

Figure 5:
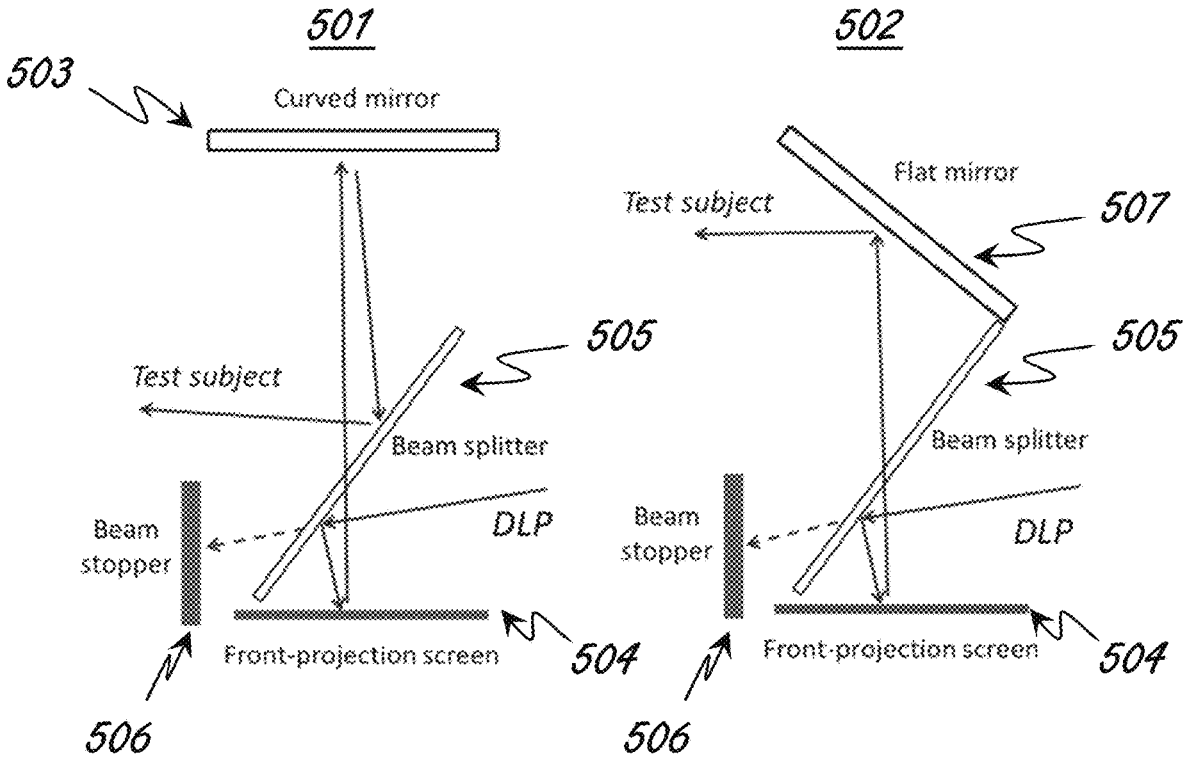
FIG. 5 illustrates two possible configurations of the instrument for near and far vision testing utilizing a beam splitter.

FIG. 5 illustrates another example configuration that provides a far viewing distance configuration 501 and a near viewing distance configuration 502. These configurations can be implemented in a compact device, such as the instrument 101 of FIG. 1. These configurations include a projector such as a digital light projector or DLP (not shown), a screen 504 (e.g., a front-projection screen), a beam splitter 505, a beam stopper 506, a curved mirror 503, and a flat mirror 507. In the far viewing distance configuration 501, the curved mirror 503 can be placed in the optical path to provide a virtual image of a stimuli on the screen 504 to the patient, similar to the configuration of FIG. 2. In the near viewing distance configuration 502, the flat mirror 507 can be placed in the optical path to provide a view of the screen 504 to the patient.

Figure 6:
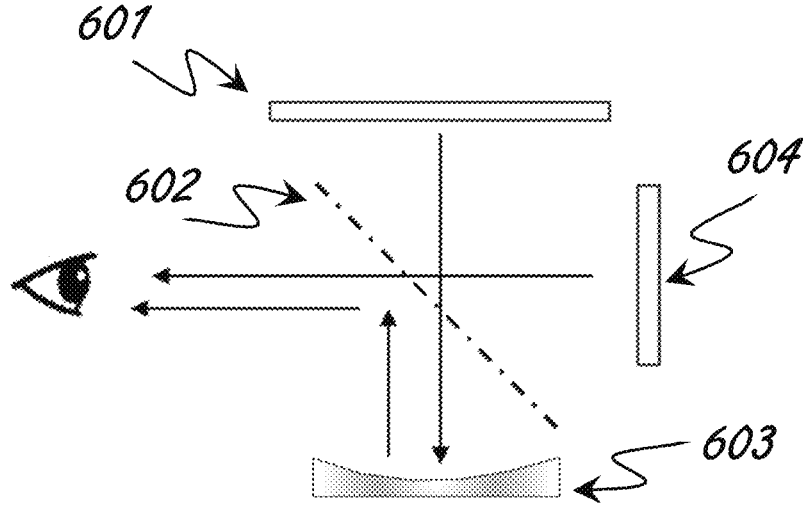
FIG. 6 illustrates a possible configuration of the instrument for near and far vision testing utilizing a beam splitter and two screens.

FIG. 6 illustrates another configuration that allows for multiple viewing distances to be provided in a single, compact device (e.g., the instrument 101 of FIG. 1). The configuration includes a first screen 601 (or monitor), a beam splitter 602, a curved mirror 603, and a second screen 604 (or monitor). One or more stimuli are presented on the first screen 601. Light from these stimuli passes through the beam splitter 602, reflects from the curved mirror 603, undergoes another reflection from the beam splitter 602, and presents to the patient at a far viewing distance. Similarly, one or more stimuli are presented on the second screen 604. Light from these stimuli passes through the beam splitter 602 and presents to the patient at a near viewing distance. In this configuration, no mechanical motion needs to be performed to switch the instrument configuration between the two viewing distances. A possible advantage of such an arrangement is the ability to quickly switch between viewing distances for the purpose of evaluating the accommodation speed of the tested patient or the subject.

It should be understood that although a limited number of example configurations have been explicitly disclosed, there are a variety of variations on these example embodiments that are within the scope of this disclosure. Variations can be accomplished using different arrangements of monitors, projectors, lenses, screens, flat mirrors, curved mirrors, beam splitters, and prisms. Such components can be arranged and manipulated in a way to provide one or more viewing distances in a compact device, such as the instrument 101 of FIG. 1.

Color Vision Testing

Cone-specific contrast can be computed from the cone excitations ($E_L$, $E_M$, $E_S$) based on psychophysically derived cone sensitivities by measuring the display luminance (Y) and CIE chromaticity (x and y):

$$E_L = Y\left[0.15514\frac{x}{y} + 0.54312 - 0.03286\frac{1-x-y}{y}\right],$$

$$E_M = Y\left[-0.15514\frac{x}{y} + 0.45684 + 0.03286\frac{1-x-y}{y}\right],$$

$$E_S = Y\left[0.00801\frac{1-x-y}{y}\right].$$

From the individual cone excitations from test and background images, the cone contrast (CC) can be computed as a Weber contrast, i.e., the difference between the cone excitations from the test image and the gray image (R/G/B=0.7843) divided by the cone excitation from the background image:

$$CC_i\ (\%) = \frac{E_i - E_{gray}}{E_{gray}} \times 100,\ (i = L, M, S).$$

In some embodiments, it can be advantageous to have a grey background image. In certain embodiments, it can be advantageous to adjust the hue of the background image to increase the measurement range or resolution or both. As an example, using a slightly red hue of the background can be advantageous while testing S-cones and a slightly blue hue of the background can be advantageous while testing the L-cones.

Most conventional 8-bit displays generally do not provide sufficient resolution for testing color vision down to physiologically achievable levels of humans. Accordingly, disclosed herein are configurations, solutions, or modifications configured to achieve high resolution color testing to reduce the achievable contrast level.

Figure 7:
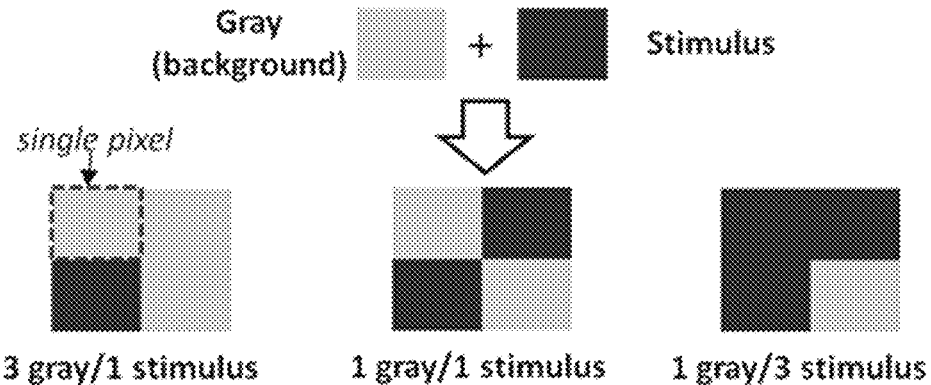
FIG. 7 illustrates a spatial dithering scheme to achieve high color resolution of the visual stimuli.

In some embodiments, to reduce the minimum color contrast level it can be advantageous to introduce spatial dithering in contrast images for L, M, or S cones. The human eye averages neighboring pixels to detect color when spacing between dithered pixels is smaller than the spatial/angular resolution of the eye. Spatial dithering with the 2 by 2 base unit may not cause issues due to pixelation. FIG. 7 illustrates a spatial dithering procedure that can be used to increase the color contrast resolution of an instrument configured for automated vision testing, such as the instrument 101 of FIG. 1. For example, it can be possible to apply the 1-gray/1-stimulus dither with the gray image (R/G/B=0.7843) and the M-cone-targeting stimulus image (R=0.7811, G=0.7866, B=0.7841) to create a checkerboard stimulus image, which in principle should provide L/M/S contrasts of −0.07%, 0.20%, and 0.01%, respectively, based on the measurements from the un-dithered image.

In some embodiments, a projector capable of displaying 10-bit color depth can be used for color contrast measurement. In certain embodiments, a 10-bit color depth monitor can be used for color contrast measurements. In various embodiments, temporal dithering can be advantageous to achieve the color resolution needed for high fidelity color vision testing.

In some embodiments, it can be advantageous to have only two colors on a screen at the same time. In such embodiments, it can be possible to use a programmable 12-bit LED driver board. The LED driver may rapidly switch LEDs between two 12-bit outputs: one for background color and another for the foreground color. The driver module may quickly switch between background and foreground and, when the foreground is displayed, the LED outputs the foreground colors, while when the background is displayed the LED driver can be switched to background colors. In this scheme, the color can be fully controlled with the LED driver using pulse width modulation, while the shape and size of the presented stimuli is determined by the projector, such as a DLP, LCD, or another such projector. A typical DLP projector is capable of switching between two frames with a frequency of about 4 kHz, and the typical pulse width modulation frequency of LEDs can be in a range of about 30 kHz.

In some embodiments, it can be advantageous to generate high resolution color stimuli by overlaying images from two or more projectors. For example, one of the projectors can be used for coarse tuning of the color while the other projector (with a neutral density (ND) filter compressing its dynamic range) can be used for fine tuning.

Figure 8:
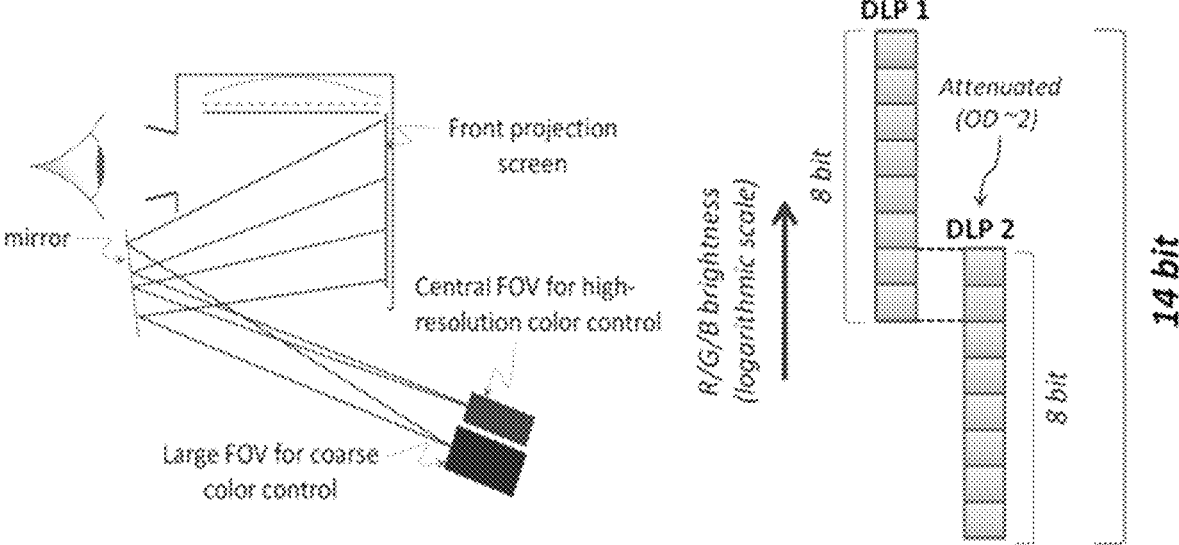
FIG. 8 illustrates a method of combining two projectors to achieve high color resolution of the visual stimuli.

FIG. 8 illustrates an example configuration using such a configuration (e.g., using two or more projectors) that can be implemented in a compact instrument, such as the instrument 101 of FIG. 1. As an example, using a ND filter with optical density (OD) of 2 (or 1% transmission), the luminosity change affected by the most significant bit of the attenuated 8-bit-per-channel projector is approximately equivalent to that of the 2nd least significant bit ($\frac{1}{2}^7 \approx 0.008$) of the unattenuated projector, assuming the projectors are identical and illuminating the same area. Therefore, the two-projector configuration with an ND filter (OD=2) can provide a combined color resolution up to 14 bits per channel.

Internal Calibration

Figure 9:
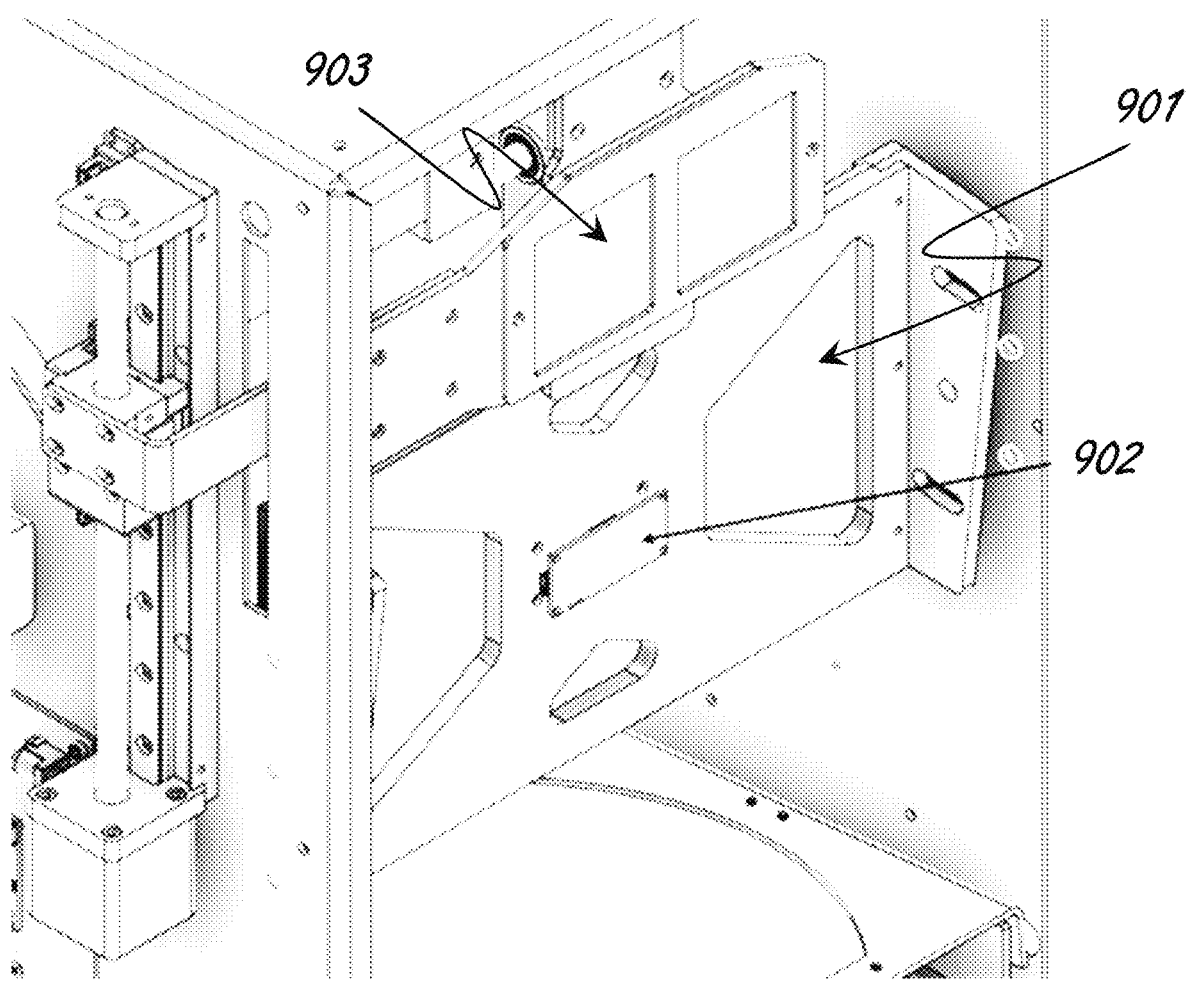
FIG. 9 illustrates a possible location of a calibration sensor behind a projector screen.

In some embodiments, it can be advantageous to monitor the spectral output and the intensity of the projection system or the display for presenting stimuli to the subject. A power meter, a spectrometer, a multispectral sensor, or any combination of such instruments can be used for continuous or periodic verification or calibration of the instrument. In some embodiments, it can be advantageous to use optical elements to direct the light from the display or the projection system to the internal calibration sensor. In various embodiments, it can be advantageous to place the sensor behind the projection screen to capture the light that is scattered through the screen. FIG. 9 illustrates an example of such an embodiment, which may be implemented in a device for automated vision testing, such as the instrument 101 of FIG. 1. A screen 901 is constructed in such a manner that some of the light projected onto the screen is allowed to pass through. The light can be detected by a sensor 902. The sensor 902 can be a single photodiode or a colorimeter sensor with a plurality of detectors sensitive to different wavelengths. In some implementations, the sensor 902 can be a spectrometer. The sensor 902 can be used for calibration verification, for internal calibration, or both. The sensor 902 can be replaceable with or without the screen 901, so that the calibration and maintenance of the device can be performed by a simple sensor replacement. In such embodiments, the sensor-screen combination can be associated with its own calibration file, which can be uploaded into the instrument software when the sensor is replaced. In some embodiments, it can be beneficial to enable stereo and ocular motility testing by equipping the device with shutters 903, such as liquid crystal (LC) shutters.

Dual Projection System

In some embodiments, it can be advantageous to use a projection system with two projectors to create a projection system that has a high resolution in the central area and a large field of view. One projector may provide a high-resolution image, while the other projector can be used for a wide field-of-view (FOV) image.

A special design of the projection screen can be beneficial for high resolution projection. In some embodiments, the screen can include a combination of transparent, opaque, and scattering layers to increase or maximize the screen resolution and/or to reduce or minimize glare. In certain embodiments, it can be beneficial to use a screen in a format such that the some of the light passes through the screen (e.g., as described herein with reference to FIG. 9). The light can be detected using a calibration sensor which can be used for checking the color and intensity calibration of the instrument and for performing internal calibration.

In some embodiments, a high resolution near field testing may not be needed and the far and near vision testing can be performed using a single projector that can be reconfigured between two orientations.

In some embodiments, it can be advantageous to passively or actively cool one or more of the projection devices or the displays in order to achieve a stable color composition of presented stimuli. A possible control mechanism for thermal management can be based on a temperature feed forward (TFF), luminous flux feedback (FFB), flux feedback and temperature feed forward (FFB & TFF), and color coordinated feedback (CCFB). A combination of the flux feedback with the temperature feed forward approach can be used to compensate for changes in the wavelength and luminance due to the junction temperature change.

While thermal effects affecting the primary colors of the LED-illuminated DLP output can be "calibrated out" to a large extent using some of the techniques disclosed herein, additional measures can be advantageous to stabilize the operating temperature of each of the R/G/B diodes. This can be useful not only due to the varying efficiency of the stock thermal management system depending on the ambient temperature, but also to compensate for changes in the LED's heat dissipation caused by the dynamic throttling of the diode's duty cycle, which causes the diode to remain "ON" for only a part of each frame, in accordance with the specific gain setting applied. This sub-frame, gain-corrected LED timing typically allows for displaying higher bit depth images without negatively impacting the accessible frame rates. As a result, the instantaneous throughput of the thermal management system can be varied to ensure that the average junction temperature is tightly controlled. The extent of the allowable temperature variance may depend on the specific type of LED emitter. Among the most common technologies used for high-power illumination diodes are two wide-bandgap III-V compound semiconductors, GaN/InGaN (Indium Gallium Nitride) and InGaAlP (Indium Gallium Aluminum Phosphide). It is the devices based on the latter technology that may exhibit an appreciable level of thermally induced drift (up to 0.7%/° C.), whereas GaN diode's output stability is approximately an order of magnitude better. InGaAlP emitters are more commonly found in the Red emitters of the RGB illumination systems.

Possible methods for cooling the LED light engines in DLP projectors may involve the attachment of the LED package's thermal plane directly to a copper heat spreader block, which is, in turn, connected via several heat pipes to a fan-cooled finned radiator. In some embodiments, it can be advantageous to augment the passive heat pipe thermal transport system by adding an active thermoelectric heat pump based on a Peltier-effect thermoelectric module (TEM).

In certain embodiments, it can be advantageous to use an LCD screen or other type of screen for color testing. In such designs, it can be advantageous to use the DLP projectors for visual acuity measurement at near and far viewing distance testing and have a dedicated LCD screen for color contrast testing. The color contrast can be measured at 14-inch near vision distance, or the subject can be asked to sit back to increase the distance. In such geometry, there is also a possibility of omitting the large FOV projector and performing the stereo and motility tests using the LCD screen.

System Architecture

Figure 10:
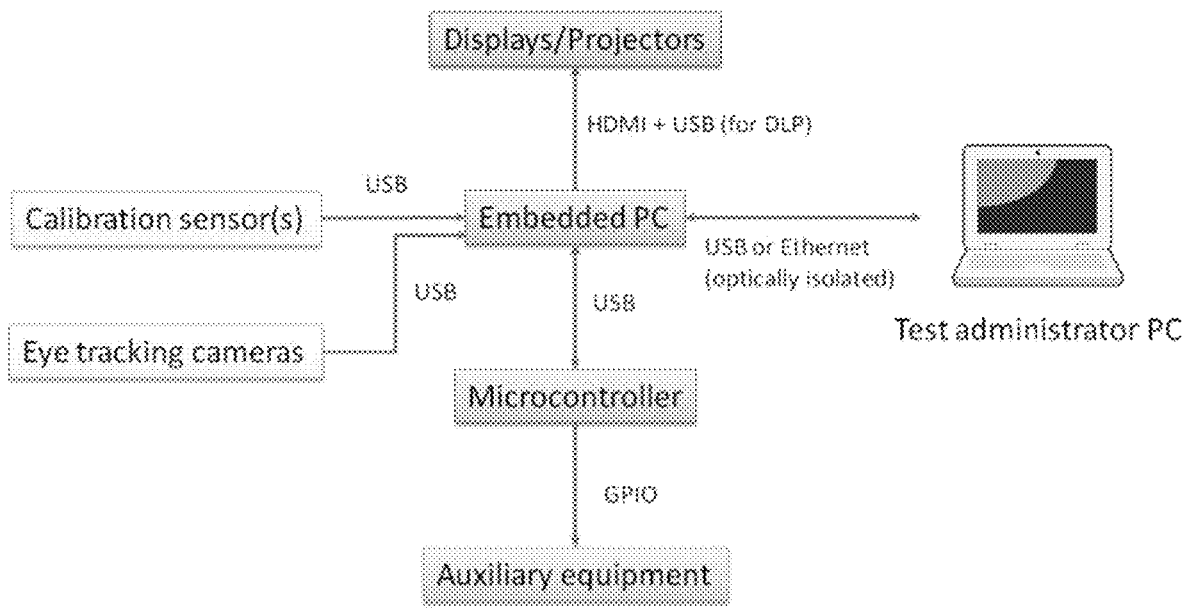
FIG. 10 illustrates two possible instrument architectures.
Figure 10:
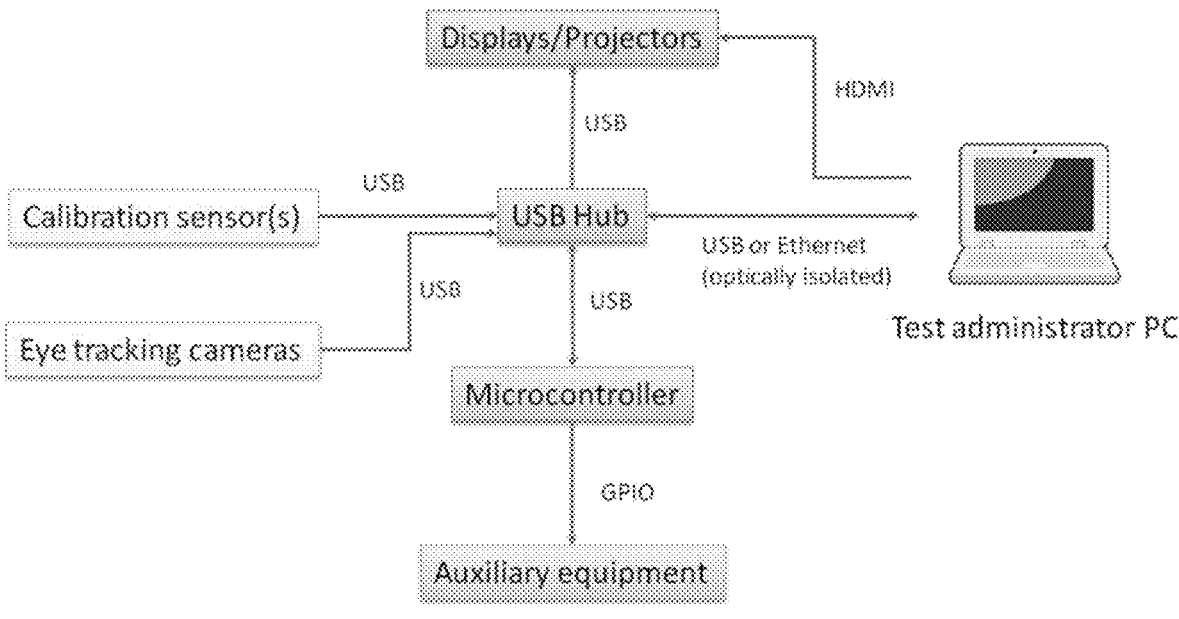

FIG. 10 illustrates examples of system architectures for various embodiments of the disclosed automated vision testing instruments and procedures, such as the instrument 101 of FIG. 1. A first architecture 1001 of the instrument is comprised of a test administrator PC, an embedded PC, displays and/or projector units, a microcontroller board, calibration sensors, and a number of auxiliary components such as LC shutters, servo motors, etc.

In the first architecture 1001, the test administrator PC contains the high-level software and it may specify which vision tests the instrument is running and what the parameters are for each test. The test administrator PC can be a desktop or a laptop located next to an instrument and connected via a USB or Ethernet cable. The embedded PC can be integrated within the instrument. A possible role of the embedded PC can be to provide drivers for the displays, projectors, microcontrollers, eye tracking cameras, and other auxiliary equipment. The microcontroller board can be responsible for operating auxiliary equipment such as the stepper motors for moving mirrors and calibration sensors, temperature sensors, etc.

A second architecture 1002 replaces the embedded PC of the first architecture 1001 with a USB hub. In this configuration, the test administrator PC performs all of the controls and also connects to the displays/projectors via an HDMI or display port cables.

Additional Aspects

In some embodiments, it can be beneficial to enable stereo and ocular motility testing by equipping the device with liquid crystal (LC) shutters (e.g., as in FIG. 9). These shutters can be synchronized with one or both of the projectors or monitors so that the projector frames can be selectively presented to the left eye or the right eye of the patient. A number of vision tests can be performed while shutters are placed in front of the patient's eyes. These tests include, but are not limited to, binocular vision evaluation, stereo vision testing, phoria testing, vergence range testing, suppression testing, and others.

In a vision testing system it can be beneficial to allow the users to create their own tests and exams. In such systems, a software development kit or API can be used to allow the users and software developers to create their own tests. It can be beneficial to allow the users to combine different vision tests into exams. The exam may consist of a pre-defined sequence of tests. Additionally, the exam sequence may depend on a subject's or patient's response to some of the tests in the exam. For example, the patient can be tested for visual acuity and only if they are able to pass with a certain score, they will be allowed to proceed with other tests within the exam sequence. It can be beneficial to assign passing and failing scores depending on the exam. In such cases, a report can be generated showing pass or fail values for the entire exam or for some portions of the exam.

It can be beneficial to store the data in a database contained within the instrument software or to pass the data to an external database.

In some aspects, the disclosed devices and methods can include additional features including but not limited to the following: ocular occluders, which can be used to cover one of the eyes of the patient to test the vision in the non-occluded eye; eye tracking using cameras, non-imaging photodiodes, or any other methods that can detect eye motion or measure eye position; mirrors, prisms, or lenses positioned near the eye which may simplify vision testing for people wearing bifocal or progressive lenses; lenses, lens combinations, or prisms which can be placed in front of the eyes either manually or using a motorized mechanism; provisions to attach trial lens frames to the front of the instrument; provisions to attach a phoropter to the front of the instrument; speech recognition software; pupil measuring devices; interpupillary distance measurement devices; internal LEDs to possibly simulate glare conditions; speakers and/or headphone jacks; ability to display grids such as the Amsler grid or an alternative method of testing retinal irregularities; ability to test visual acuity, contrast sensitivity, color contrast, stereo acuity, horizontal phoria, vertical phoria, vergence range, and other aspects of vision.

In the present disclosure the terms subject, test subject, patient, and viewer can be used interchangeably.

The present disclosure describes various features, no single one of which is solely responsible for the benefits described herein. It will be understood that various features described herein can be combined, modified, or omitted, as would be apparent to one of ordinary skill. Other combinations and sub-combinations than those specifically described herein will be apparent to one of ordinary skill, and are intended to form a part of this disclosure. Various methods are described herein in connection with various flowchart steps and/or phases. It will be understood that in many cases, certain steps and/or phases can be combined together such that multiple steps and/or phases shown in the flowcharts can be performed as a single step and/or phase. Also, certain steps and/or phases can be broken into additional sub-components to be performed separately. In some instances, the order of the steps and/or phases can be rearranged and certain steps and/or phases can be omitted entirely. Also, the methods described herein are to be understood to be open-ended, such that additional steps and/or phases to those shown and described herein can also be performed.

Some aspects of the systems and methods described herein can advantageously be implemented using, for example, computer software, hardware, firmware, or any combination of computer software, hardware, and firmware. Computer software can comprise computer executable code stored in a computer readable medium (e.g., non-transitory computer readable medium) that, when executed, performs the functions described herein. In some embodiments, computer-executable code is executed by one or more general purpose computer processors. A skilled artisan will appreciate, in light of this disclosure, that any feature or function that can be implemented using software to be executed on a general purpose computer can also be implemented using a different combination of hardware, software, or firmware. For example, such a module can be implemented completely in hardware using a combination of integrated circuits. Alternatively or additionally, such a feature or function can be implemented completely or partially using specialized computers designed to perform the particular functions described herein rather than by general purpose computers.

Multiple distributed computing devices can be substituted for any one computing device described herein. In such distributed embodiments, the functions of the one computing device are distributed (e.g., over a network) such that some functions are performed on each of the distributed computing devices.

Some embodiments can be described with reference to equations, algorithms, and/or flowchart illustrations. These methods can be implemented using computer program instructions executable on one or more computers. These methods may also be implemented as computer program products either separately, or as a component of an apparatus or system. In this regard, each equation, algorithm, block, or step of a flowchart, and combinations thereof, can be implemented by hardware, firmware, and/or software including one or more computer program instructions embodied in computer-readable program code logic. As will be appreciated, any such computer program instructions can be loaded onto one or more computers, including without limitation a general purpose computer or special purpose computer, or other programmable processing apparatus to produce a machine, such that the computer program instructions which execute on the computer(s) or other programmable processing device(s) implement the functions specified in the equations, algorithms, and/or flowcharts. It will also be understood that each equation, algorithm, and/or block in flowchart illustrations, and combinations thereof, can be implemented by special purpose hardware-based computer systems which perform the specified functions or steps, or combinations of special purpose hardware and computer-readable program code logic means.

Furthermore, computer program instructions, such as embodied in computer-readable program code logic, may also be stored in a computer readable memory (e.g., a non-transitory computer readable medium) that can direct one or more computers or other programmable processing devices to function in a particular manner, such that the instructions stored in the computer-readable memory implement the function(s) specified in the block(s) of the flowchart(s). The computer program instructions may also be loaded onto one or more computers or other programmable computing devices to cause a series of operational steps to be performed on the one or more computers or other programmable computing devices to produce a computer-implemented process such that the instructions which execute on the computer or other programmable processing apparatus provide steps for implementing the functions specified in the equation(s), algorithm(s), and/or block(s) of the flowchart(s).

Some or all of the methods and tasks described herein can be performed and fully automated by a computer system. The computer system may, in some cases, include multiple distinct computers or computing devices (e.g., physical servers, workstations, storage arrays, etc.) that communicate and interoperate over a network to perform the described functions. Each such computing device typically includes a processor (or multiple processors) that executes program instructions or modules stored in a memory or other non-transitory computer-readable storage medium or device. The various functions disclosed herein can be embodied in such program instructions, although some or all of the disclosed functions may alternatively be implemented in application-specific circuitry (e.g., ASICs or FPGAs) of the computer system. Where the computer system includes multiple computing devices, these devices may, but need not, be co-located. The results of the disclosed methods and tasks can be persistently stored by transforming physical storage devices, such as solid state memory chips and/or magnetic disks, into a different state.

Unless the context clearly requires otherwise, throughout the description and the claims, the words "comprise," "comprising," and the like are to be construed in an inclusive sense, as opposed to an exclusive or exhaustive sense; that is to say, in the sense of "including, but not limited to." The word "coupled", as generally used herein, refers to two or more elements that can be either directly connected, or connected by way of one or more intermediate elements. Additionally, the words "herein," "above," "below," and words of similar import, when used in this application, shall refer to this application as a whole and not to any particular portions of this application. Where the context permits, words in the above Detailed Description using the singular or plural number may also include the plural or singular number respectively. The word "or" in reference to a list of two or more items, that word covers all of the following interpretations of the word: any of the items in the list, all of the items in the list, and any combination of the items in the list. The word "exemplary" is used exclusively herein to mean "serving as an example, instance, or illustration." Any implementation described herein as "exemplary" is not necessarily to be construed as preferred or advantageous over other implementations.

The disclosure is not intended to be limited to the implementations shown herein. Various modifications to the implementations described in this disclosure can be readily apparent to those skilled in the art, and the generic principles defined herein can be applied to other implementations without departing from the spirit or scope of this disclosure. The teachings provided herein can be applied to other methods and systems, and are not limited to the methods and systems described above, and elements and acts of the various embodiments described above can be combined to provide further embodiments. Accordingly, the novel methods and systems described herein can be embodied in a variety of other forms; furthermore, various omissions, substitutions and changes in the form of the methods and systems described herein can be made without departing from the spirit of the disclosure. The accompanying claims and their equivalents are intended to cover such forms or modifications as would fall within the scope and spirit of the disclosure.

What is claimed is:

1. A system for performing automated vison testing, the system comprising:
   a display device system configured to present one or more stimuli to one or both eyes of a tested subject;
   an input device configured to record responses of the tested subject;
   an analysis system configured to analyze the responses and to present a result of the vision test being performed; and
   one or more optical components, wherein a plurality of stimuli viewing distances is achieved by arranging the system with different configurations of the one or more optical components,
   wherein at least one of the one or more optical components is a curved mirror,
   wherein the one or more optical components includes a second mirror, an optical path of the one or more stimuli including the curved mirror or the second mirror by actuating the curved mirror or the second mirror into and out of the optical path, and wherein a viewing distance of the system changes as a consequence of which mirror is in the optical path of the one or more stimuli.

2. The system of claim 1, wherein the second mirror is a flat mirror.

3. The system of claim 1, wherein at least one of the one or more optical components is a flat mirror that is configured in a manner so that it can be rotated about an axis, the axis parallel to the surface of the flat mirror.

4. The system of claim 1, wherein the display device system includes one or more projection devices and a front projection screen, the one or more projection devices configured to project images onto the front projection screen.

5. The system of claim 4 further comprising a calibration sensor located behind the front projection screen, wherein the front projection screen is configured in such way that at least a portion of the light from the one or more projection devices passes through the front projection screen and is detected by the calibration sensor.

6. The system of claim 5, wherein the calibration sensor is a photodiode.

7. The system of claim 5, wherein the calibration sensor is a colorimeter.

8. The system of claim 5, wherein the calibration sensor is a spectrometer.

9. The system of claim 5, wherein the calibration sensor is configured to be used for calibration verification of the system or for performing an automated self-calibration of the system.

10. The system of claim 4, wherein the one or more projection devices includes a first projection device and a second projection device, the first projection device configured to project a large field image and the second projection device configured to project a small field image.

11. The system of claim 10, wherein the large field image and the small field image overlap.

12. The system of claim 4, wherein the one or more projection devices includes a first projection device and a second projection device, the first projection device configured to have a first value of maximum brightness and the second projection device configured to have a second value of maximum brightness that is different from the first value of maximum brightness.

13. The system of claim 1 further comprising optical shutters positioned in front of an eye of the tested subject.

14. The system of claim 13, wherein the optical shutters are liquid crystal shutters.

15. A system for performing automated vison testing, the system comprising:
   a display device system configured to present one or more stimuli to one or both eyes of a tested subject;
   an input device configured to record responses of the tested subject; and
   an analysis system configured to analyze the responses and to present a result of the vision test being performed,
   wherein the display device system includes one or more projection devices and a front projection screen, the one or more projection devices configured to project images onto the front projection screen,
   wherein the one or more projection devices includes a first projection device and a second projection device, the first projection device configured to project a large field image and the second projection device configured to project a small field image.

16. The system of claim 15, wherein the large field image and the small field image overlap.

17. The system of claim 15 further comprising one or more optical components, wherein a plurality of stimuli viewing distances is achieved by arranging the system with different configurations of the one or more optical components.

18. A system for performing automated vison testing, the system comprising:
   a display device system configured to present one or more stimuli to one or both eyes of a tested subject;
   an input device configured to record responses of the tested subject; and
   an analysis system configured to analyze the responses and to present a result of the vision test being performed,
   wherein the display device system includes one or more projection devices and a front projection screen, the one or more projection devices configured to project images onto the front projection screen,
   wherein the one or more projection devices includes a first projection device and a second projection device, the first projection device configured to have a first value of maximum brightness and the second projection device configured to have a second value of maximum brightness that is different from the first value of maximum brightness.

19. The system of claim 18 further comprising one or more optical components, wherein a plurality of stimuli viewing distances is achieved by arranging the system with different configurations of the one or more optical components.

20. The system of claim 18 further comprising a calibration sensor located behind the front projection screen, wherein the front projection screen is configured in such way that at least a portion of the light from the one or more projection devices passes through the front projection screen and is detected by the calibration sensor.

* * * * *